(12) United States Patent
Shin et al.

(10) Patent No.: US 7,851,180 B2
(45) Date of Patent: Dec. 14, 2010

(54) MICROORGANISM PRODUCING L-METHIONINE PRECURSOR AND THE METHOD OF PRODUCING L-METHIONINE PRECURSOR USING THE MICROORGANISM

(75) Inventors: Young Uk Shin, Gyeonggi-do (KR); So Young Kim, Gyeonggi-do (KR); Jin Sook Chang, Seoul (KR); Young Wook Cho, Seoul (KR); Han Jin Lee, Seoul (KR); In Kyung Heo, Seoul (KR); Kwang Ho Na, Seoul (KR); Chang Il Seo, Incheon (KR); Chul Ha Kim, Seoul (KR); Hye Won Um, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 133 days.

(21) Appl. No.: 12/062,927

(22) Filed: Apr. 4, 2008

(65) Prior Publication Data

US 2009/0253187 A1    Oct. 8, 2009

(51) Int. Cl.
*C12N 1/12*    (2006.01)
*C12N 1/20*    (2006.01)
*C12P 1/00*    (2006.01)
(52) U.S. Cl. .................. 435/41; 435/252.1; 435/252.33
(58) Field of Classification Search ........................ None
See application file for complete search history.

(56) References Cited

U.S. PATENT DOCUMENTS

| 2002/0049305 | A1 | 4/2002 | Bathe et al. | |
|---|---|---|---|---|
| 2003/0092026 | A1 | 5/2003 | Rey et al. | |
| 2005/0054060 | A1 | 3/2005 | Chateau et al. | |
| 2009/0029424 | A1* | 1/2009 | Bestel-Corre et al. | ....... 435/113 |

FOREIGN PATENT DOCUMENTS

| JP | 2000-139471 | A  | 5/2000 |
|---|---|---|---|
| KR | 10-1992-0008365 | B1 | 9/1992 |
| WO | 2004/035617 | A2 | 4/2004 |
| WO | 2005/075625 | A1 | 8/2005 |
| WO | 2005108561 | A2 | 11/2005 |
| WO | 2007/077041 | A1 | 7/2007 |
| WO | 2008013432 | A1 | 1/2008 |
| WO | 2008/127240 | A1 | 10/2008 |
| WO | 2008127240 | A1 | 10/2008 |

OTHER PUBLICATIONS

Mischoulon et al., Role of S-adenosyl-L-methionine in the treatment of depression: a review of the evidence, American Journal of Clinical Nutrition, 2002, vol. 76, pp. 1158S-1161S.
Mato et al., S-Adenosylmethionine: a control switch that regulates liver function, FASEB, 2002, vol. 16(1), pp. 15-26.
Biran et al., Control of methionine biosynthesis in *Escherichia coli* by proteolysis, Molecular Microbiology, 2000, vol. 37(6), pp. 1436-1443.
Kromer et al., Accumulation of homolanthionine and activation of a novel pathway for isoleucine biosynthesis in corynebacterium glutamicum McbR deletion strains, Journal of Bacteriology, 2006, vol. 188(2), pp. 609-618.
Jensen et al., Artificial promoters for metabolic optimization, Biotechnology and Bioengineering, 1998, vol. 58(2-3), pp. 191-195.
Carrier et al., Library of synthetic 5' secondary structures to manipulate mRNA stability in *Escherichia coli*, Biotechnology Progress, 1999, vol. 15, pp. 58-64.
Franch et al., U-turns and regulatory RNAs, Current Opinion in Microbiology, 2000, vol. 3, pp. 159-164.
Qiu et al., The *Escherichia coli* polB locus is identical to dinA, the structural gene for DNA polymerase II, The Journal of Biological Chemistry, 1997, vol. 272(13), pp. 8611-8617.
Yano et al., Directed evolution of an aspartate aminotransferase with new substrate specificities, Proceedings of the National Academy of Science, USA, 1998, vol. 95, pp. 5511-5515.
Wente et al., Different amino acid substitutions at the same position in the nucleotide-binding site of aspartate transcarbamoylase have diverse effects on the allosteric properties of the enzyme, The Journal of Biological Chemistry, 1991, vol. 266(31), pp. 20833-20839.
Jeon et al., S-adenosylmethionine protects post-ischemic mitochondrial injury in rat liver, Journal of Hepatology, 2001, vol. 34, pp. 395-401.
Datsenko et al., One-step inactivation of chromosomal genes in *Escherichia coli* K-12 using PCR products, PNAS 2000, vol. 97(12), pp. 6640-6645.
Blattner, et al., The Complete Genome Sequence of *Escherichia coli* K-12, Science, 277(5):1453-1462, 1997.

* cited by examiner

*Primary Examiner*—Mark Navarro
(74) *Attorney, Agent, or Firm*—Seed IP Law Group PLLC

(57) ABSTRACT

The present invention relates to a microorganism producing L-methionine precursor, O-succinylhomoserine, and a method of producing L-methionine precursor using the microorganism,

20 Claims, 3 Drawing Sheets

SEQUENCE LISTING

<160> NUMBER OF SEQ ID NOS: 30

<210> SEQ ID NO 1
<211> LENGTH: 70
<212> TYPE: DNA
<213> ORGANISM: Artificial Sequence
<220> FEATURE:
<223> OTHER INFORMATION: primer for amplification of Chloramphenichol

<400> SEQUENCE: 1

TTACTCTGGT GCCTGACATT TCACCGACAA AGCCCAGGGA ACTTCATCAC gtgtaggctg    60

Gagctgcttc    70

<210> SEQ ID NO 2
<211> LENGTH: 70
<212> TYPE: DNA
<213> ORGANISM: Artificial Sequence
<220> FEATURE:
<223> OTHER INFORMATION: primer for amplification of Chloramphenichol

<400> SEQUENCE: 2

TTACCCCTTG TTTGCAGCCC GGAAGCCATT TTCCAGGTCG GCAATTAAAT catatgaata    60

Tcctccttag    70

<210> SEQ ID NO 3
<211> LENGTH: 70
<212> TYPE: DNA
<213> ORGANISM: Artificial Sequence
<220> FEATURE:
<223> OTHER INFORMATION: primer for amplification of kanamycin

<400> SEQUENCE: 3

```
AAAGAATATG CCGATCGGTT CGGGCTTAGG CTCCAGTGCC TGTTCGGTGG gtgtaggctg      60
gagctgcttc                                                             70
```

<210> SEQ ID NO 4
<211> LENGTH: 70
<212> TYPE: DNA
<213> ORGANISM: Artificial Sequence
<220> FEATURE:
<223> OTHER INFORMATION: primer for amplification of kanamycin

<400> SEQUENCE: 4

```
AGACAACCGA CATCGCTTTC AACATTGGCG ACCGGAGCCG GGAAGGCAAA catatgaata      60
tcctccttag                                                             70
```

<210> SEQ ID NO 5
<211> LENGTH: 71
<212> TYPE: DNA
<213> ORGANISM: Artificial Sequence
<220> FEATURE:
<223> OTHER INFORMATION: primer for amplification of Chloramphenichol

<400> SEQUENCE: 5

```
atggctgaat ggagcggcga atatatcagc ccatacgctg agcacggcaa ggtgtaggct      60
ggagctgctt c                                                           71
```

<210> SEQ ID NO 6
<211> LENGTH: 65
<212> TYPE: DNA
<213> ORGANISM: Artificial Sequence
<220> FEATURE:
<223> OTHER INFORMATION: primer for amplification of Chloramphenichol

<400> SEQUENCE: 6

```
gtattcccac gtctccgggt taatccccat ctcacgcatg atctccatat gaatatcctc      60
cttag                                                                  65
```

<210> SEQ ID NO 7
<211> LENGTH: 19
<212> TYPE: DNA
<213> ORGANISM: Escherichia coli
<220> FEATURE:
<223> OTHER INFORMATION: primer for amplification of metJ

<400> SEQUENCE: 7

```
gggctttgtc ggtgaaatg                                                   19
```

<210> SEQ ID NO 8
<211> LENGTH: 19
<212> TYPE: DNA
<213> ORGANISM: Escherichia coli
<220> FEATURE:
<223> OTHER INFORMATION: primer for amplification of metJ

<400> SEQUENCE: 8

```
actttgcgat gagcgagag                                                   19
```

<210> SEQ ID NO 9
<211> LENGTH: 70
<212> TYPE: DNA
<213> ORGANISM: Artificial Sequence
<220> FEATURE:
<223> OTHER INFORMATION: primer for deletion of metA

<400> SEQUENCE: 9

```
CAATTTCTTG CGTGAAGAAA ACGTCTTTGT GATGACAACT TCTCGTGCGT gtgtaggctg      60

Gagctgcttc                                                            70
```

<210> SEQ ID NO 10
<211> LENGTH: 70
<212> TYPE: DNA
<213> ORGANISM: Artificial Sequence
<220> FEATURE:
<223> OTHER INFORMATION: primer for deletion of metA

<400> SEQUENCE: 10

```
AATCCAGCGT TGGATTCATG TGCCGTAGAT CGTATGGCGT GATCTGGTAG catatgaata      60

Tcctccttag                                                            70
```

<210> SEQ ID NO 11
<211> LENGTH: 28
<212> TYPE: DNA
<213> ORGANISM: Escherichia coli
<220> FEATURE:
<223> OTHER INFORMATION: primer for amplification of metA

<400> SEQUENCE: 11

```
aatggatccT GCCGTGAGCG GCGAATAC                                        28
```

<210> SEQ ID NO 12
<211> LENGTH: 28
<212> TYPE: DNA
<213> ORGANISM: Escherichia coli
<220> FEATURE:
<223> OTHER INFORMATION: primer for amplification of metA

<400> SEQUENCE: 12

```
agctctagaC TGCTGAGGTA CGTTTCGG                                        28
```

<210> SEQ ID NO 13
<211> LENGTH: 930
<212> TYPE: DNA
<213> ORGANISM: Escherichia coli

<400> SEQUENCE: 13

```
atgccgattc gtgtgccgga cgagctaccc gccgtcaatt tcttgcgtga agaaaacgtc      60
tttgtgatga caactctcg tgcgtctggt caggaaattc gtccgcttaa ggttctgatc     120
cttaacctga tgccgaagaa gattgaaact gaaaatcagt ttctgcgcct gctttcaaac    180
tcacctttgc aggtcgatat tcagctgttg cgcatcgatt cccgtgaatc gcgcaacacg    240
cccgcagagc atctgaacaa cttctactgt aactttgaag atattcagga tcagaacttt    300
gacggtttga ttgtaactgg tgcgccgctg ggcctggtgg agtttaatga tgtcgcttac    360
tggccgcaga tcaaacaggt gctggagtgg tcgaaagatc acgtcacctc gacgctgttt    420
gtctgctggg cggtacaggc cgcgctcaat atcctctacg gcattcctaa gcaaactcgc    480
accgaacaac tctctggcgt ttacgagcat catattctcc atcctcatgc gcttctgacg    540
```

```
cgtggctttg atgattcatt cctggcaccg cattcgcgct atgctgactt tccggctgcg    600
ttgattcgtg attacaccga tctggaaatt ctggcagaga cggaagaagg ggatgcatat    660
ctgttagcca gtaaagataa gcgcattgcc tttgtgacgg ccatcccga atatgatgcg    720 caaacgctgg cgcaggaatt tttccgcgat gtggaagccg gactagaccc ggatgtaccg    780
tataactatt tcccgcacaa tgatccgcaa atacaccgc gagcgagctg cgtagtcac     840 ggtaatttac tgtttaccaa ctggctcaac tattacgtct accggatcac gccatacgat    900
ctacggcaca tgaatccaac gctggattaa                                    930
```

```
<210> SEQ ID NO 14
<211> LENGTH: 309
<212> TYPE: PRT
<213> ORGANISM: Escherichia coli

<400> SEQUENCE: 14

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Gln Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Leu Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Arg Ile Thr Pro Tyr Asp Leu Arg His Met
    290                 295                 300
```

Asn Pro Thr Leu Asp
305

<210> SEQ ID NO 15
<211> LENGTH: 930
<212> TYPE: DNA
<213> ORGANISM: Escherichia coli

<400> SEQUENCE: 15

```
atgccgattc gtgtgccgga cgagctaccc gccgtcaatt tcttgcgtga agaaaacgtc      60
tttgtgatgt caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt ctcgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
ttgattcgtg attacaccga tctggaaatt ctggcagaga cggaagaagg ggatgcatat     660
ctgtttgcca gtaaagataa gcgcattgcc tttgtgacgg gccatccgaa atatgatgcg     720
caaacgctgg cgcaggaatt tttccgcgat gtggaagccg actagaccc  ggatgtaccg     780
tataactatt ccccgcacaa tgatccgcaa atacaccgc  gagagagctg gcgtagtcac     840
ggtaatttac tgtttaccaa ctggctcaac tattacgtct accagatcgc gccatacgat     900
ctacggcaca tgtatccaac gctggattaa                                      930
```

<210> SEQ ID NO 16
<211> LENGTH: 309
<212> TYPE: PRT
<213> ORGANISM: Escherichia coli

<400> SEQUENCE: 16

```
Met Pro Ile Arg Val Pro Asp Glu Leu Pro Ala Val Asn Phe Leu Arg
1               5                   10                  15

Glu Glu Asn Val Phe Val Met Ser Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
```

-continued

```
                145                 150                 155                 160
Thr Glu Lys Leu Ser Gly Val Tyr Glu His His Ile Leu His Pro His
                    165                 170                 175

Ala Leu Leu Thr Arg Gly Phe Asp Asp Ser Phe Leu Ala Pro His Ser
                180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Gly Asp Ala Tyr Leu Phe Ala Ser
        210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Glu Ser Trp Arg Ser His Gly Asn Leu Leu Phe Thr Asn Trp
        275                 280                 285

Leu Asn Tyr Tyr Val Tyr Gln Ile Ala Pro Tyr Asp Leu Arg His Met
    290                 295                 300

Tyr Pro Thr Leu Asp
305
```

<210> SEQ ID NO 17
<211> LENGTH: 930
<212> TYPE: DNA
<213> ORGANISM: Escherichia coli

<400> SEQUENCE: 17

```
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgttt     420
gtctgctggg cggtacaggc cgcgctcaac atcctctacg cattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
ttgattcgtg attacaccga tctggaaatt ctggcagaga cggaagaagg ggatgcatat     660
ctgtttgcca gtaaagataa gcgcattgcc tttgtgacgg gccatccgga atatgatgcg     720
caaacgctgg cgcaggaatt tttccgcgat gtggaagccg gactagaccc ggatgtaccg     780
tataactatt tcccgcacaa tgatccgcaa aatacaccgc gagcgagctg cgtagtcac     840
ggtaatttac tgtttaccaa ctggctccac tattacgtct accagatcac gccatacgat     900
ctacggcaca tgaatccaac gctggattaa                                     930
```

<210> SEQ ID NO 18
<211> LENGTH: 309
<212> TYPE: PRT
<213> ORGANISM: Escherichia coli

<400> SEQUENCE: 18

```
Met Pro Ile Arg Val Pro Asp Glu Leu Pro Ala Val Asn Phe Leu Arg
1               5                   10                  15
Glu Glu Asn Val Phe Val Met Thr Thr Ser Arg Ala Ser Gly Gln Glu
            20                  25                  30
Ile Arg Pro Leu Lys Val Leu Ile Leu Asn Leu Met Pro Lys Lys Ile
        35                  40                  45
Glu Thr Glu Asn Gln Phe Leu Arg Leu Leu Ser Asn Ser Pro Leu Gln
    50                  55                  60
Val Asp Ile Gln Leu Leu Arg Ile Asp Ser Arg Glu Ser Arg Asn Thr
65                  70                  75                  80
Pro Ala Glu His Leu Asn Asn Phe Tyr Cys Asn Phe Glu Asp Ile Gln
                85                  90                  95
Asp Gln Asn Phe Asp Gly Leu Ile Val Thr Gly Ala Pro Leu Gly Leu
            100                 105                 110
Val Glu Phe Asn Asp Val Ala Tyr Trp Pro Gln Ile Lys Gln Val Leu
        115                 120                 125
Glu Trp Ser Lys Asp His Val Thr Ser Thr Leu Phe Val Cys Trp Ala
    130                 135                 140
Val Gln Ala Ala Leu Asn Ile Leu Tyr Gly Ile Pro Lys Gln Thr Arg
145                 150                 155                 160
Thr Glu Lys Leu Ser Gly Val Tyr Glu His His Ile Leu His Pro His
                165                 170                 175
Ala Leu Leu Thr Arg Gly Phe Asp Asp Ser Phe Leu Ala Pro His Ser
            180                 185                 190
Arg Tyr Ala Asp Phe Pro Ala Ala Leu Ile Arg Asp Tyr Thr Asp Leu
        195                 200                 205
Glu Ile Leu Ala Glu Thr Glu Glu Gly Asp Ala Tyr Leu Phe Ala Ser
    210                 215                 220
Lys Asp Lys Arg Ile Ala Phe Val Thr Gly His Pro Glu Tyr Asp Ala
225                 230                 235                 240
Gln Thr Leu Ala Gln Glu Phe Phe Arg Asp Val Glu Ala Gly Leu Asp
                245                 250                 255
Pro Asp Val Pro Tyr Asn Tyr Phe Pro His Asn Asp Pro Gln Asn Thr
            260                 265                 270
Pro Arg Ala Ser Trp Arg Ser His Gly Asn Leu Leu Phe Thr Asn Trp
        275                 280                 285
Leu His Tyr Tyr Val Tyr Gln Ile Thr Pro Tyr Asp Leu Arg His Met
    290                 295                 300
Asn Pro Thr Leu Asp
305

<210> SEQ ID NO 19
<211> LENGTH: 930
<212> TYPE: DNA
<213> ORGANISM: Escherichia coli

<400> SEQUENCE: 19
atgccgattc gtgtgccgga cgagctaccc gccgtcaatt tcttgcgtga agaaaacgtc    60
tttgtgatga caacttctcg tgcgcctggt caggaaattc gtccacttaa ggttctgatc   120
cttaacctga tgccgaagaa gattgaaact gaaaatcagt ttctgcgcct gctttcaaac   180
tcacctttgc aggtcgatat tcagctgttg cgcatcgatt ccgtgaatc gcgcaacacg   240 cccgcagagc atctgaacaa cttctactgt aactttgaag atattcagga tcagaacttt   300
```

```
gacggtttga ttgtaactgg tgcgccgctg ggcctggtgg ggtttaatga tgtcgcttac    360
tggccgcaga tcaaacaggt gctggagtgg tcgaaagatc acgtcacctc gacgctgtct    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg ccatcccga atatgatgcg    720 caaacgctgg cgcaggaatt tttccgcgat gtggaagccg gactagaccc ggatgtaccg    780
tataactatt tcccgcacaa tgatccgcaa atacaccgc gagcgagctg cgtagtcac    840 ggtaatttac tgtttaccaa ctggctcaac tattacgtct accagatcac gccatacgat    900
ctacggcaca tgaacccaac gctggattaa                                     930
```

<210> SEQ ID NO 20
<211> LENGTH: 309
<212> TYPE: PRT
<213> ORGANISM: Escherichia coli

<400> SEQUENCE: 20

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Pro Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
        50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Gly Phe Asn Asp Val Ala Tyr Trp Pro Gln Ile Lys Gln Val Leu
        115                 120                 125

Glu Trp Ser Lys Asp His Val Thr Ser Thr Leu Ser Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
```

-continued

```
                    260                 265                 270
Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
        290                 295                 300

Asn Pro Thr Leu Asp
305

<210> SEQ ID NO 21
<211> LENGTH: 930
<212> TYPE: DNA
<213> ORGANISM: Escherichia coli

<400> SEQUENCE: 21
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcagcacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgatt     420
gtctgctggg cggtacaggc cgcgctcaat atcctctacg cattcctaa gcaaactcgc      480 accgaaaaac tctctggcgt ttacgagcat catattctcc atcctcatgc gcttctgacg     540
cgtggctttg atgattcatt cctggcaccg cactcgcgct atgctgactt ccggcagcg      600 ttgattcgtg attacaccga tctggaaatt ctggcagaga cggaagaagg ggatgcatat     660
ctgtttgcca gtaaagataa gcgcattgcc tttgtgacgg ccatcccga atatgatgcg     720 caaacgctgg cgcaggaatt tttccgcgat gtggaagccg actagaccc ggatgtaccg      780 tataactatt tcccgcacaa tgatccgcaa atacaccgc gagcgagctg cgtagtcac      840 ggtaatttac tgtttaccaa ctggctcaac aattacgtct accagatcac gccatacgat     900
ctacggcact tgaatccaac gctggattaa                                      930

<210> SEQ ID NO 22
<211> LENGTH: 309
<212> TYPE: PRT
<213> ORGANISM: Escherichia coli

<400> SEQUENCE: 22

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Ser Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110
```

-continued

```
Val Glu Phe Asn Asp Val Ala Tyr Trp Pro Gln Ile Lys Gln Val Leu
        115                 120                 125
Glu Trp Ser Lys Asp His Val Thr Ser Thr Leu Ile Val Cys Trp Ala
130                 135                 140
Val Gln Ala Ala Leu Asn Ile Leu Tyr Gly Ile Pro Lys Gln Thr Arg
145                 150                 155                 160
Thr Glu Lys Leu Ser Gly Val Tyr Glu His His Ile Leu His Pro His
                165                 170                 175
Ala Leu Leu Thr Arg Gly Phe Asp Asp Ser Phe Leu Ala Pro His Ser
            180                 185                 190
Arg Tyr Ala Asp Phe Pro Ala Ala Leu Ile Arg Asp Tyr Thr Asp Leu
        195                 200                 205
Glu Ile Leu Ala Glu Thr Glu Glu Gly Asp Ala Tyr Leu Phe Ala Ser
    210                 215                 220
Lys Asp Lys Arg Ile Ala Phe Val Thr Gly His Pro Glu Tyr Asp Ala
225                 230                 235                 240
Gln Thr Leu Ala Gln Glu Phe Phe Arg Asp Val Glu Ala Gly Leu Asp
                245                 250                 255
Pro Asp Val Pro Tyr Asn Tyr Phe Pro His Asn Asp Pro Gln Asn Thr
            260                 265                 270
Pro Arg Ala Ser Trp Arg Ser His Gly Asn Leu Leu Phe Thr Asn Trp
        275                 280                 285
Leu Asn Asn Tyr Val Tyr Gln Ile Thr Pro Tyr Asp Leu Arg His Leu
    290                 295                 300
Asn Pro Thr Leu Asp
305

<210> SEQ ID NO 23
<211> LENGTH: 42
<212> TYPE: DNA
<213> ORGANISM: Artificial Sequence
<220> FEATURE:
<223> OTHER INFORMATION: primer for integration of metA

<400> SEQUENCE: 23

TTTCCGAAAC GTACCTCAGC AGgtgtaggc tggagctgct tc                42

<210> SEQ ID NO 24
<211> LENGTH: 43
<212> TYPE: DNA
<213> ORGANISM: Artificial Sequence
<220> FEATURE:
<223> OTHER INFORMATION: primer for integration of metA

<400> SEQUENCE: 24

GAATAAAATT TATTCACCTG CTGcatatga atatcctcct tag               43

<210> SEQ ID NO 25
<211> LENGTH: 23
<212> TYPE: DNA
<213> ORGANISM: Escherichia coli
<220> FEATURE:
<223> OTHER INFORMATION: primer for integration of metA

<400> SEQUENCE: 25

CAGCAGGTGA ATAAATTTTA TTC                                     23

<210> SEQ ID NO 26
<211> LENGTH: 20
```

-continued

```
<212> TYPE: DNA
<213> ORGANISM: Escherichia coli
<220> FEATURE:
<223> OTHER INFORMATION: primer for integration of metA

<400> SEQUENCE: 26

CGCGAATGGA AGCTGTTTCc                                                    20

<210> SEQ ID NO 27
<211> LENGTH: 32
<212> TYPE: DNA
<213> ORGANISM: Escherichia coli
<220> FEATURE:
<223> OTHER INFORMATION: primer for amplification thrA

<400> SEQUENCE: 27

CTGGCAAAGC TTtcaaagga aaactccttc gt                                      32

<210> SEQ ID NO 28
<211> LENGTH: 32
<212> TYPE: DNA
<213> ORGANISM: Escherichia coli
<220> FEATURE:
<223> OTHER INFORMATION: primer for amplification of thrA

<400> SEQUENCE: 28

AGTCGTGATA TCatgcgagt gttgaagttc gg                                      32

<210> SEQ ID NO 29
<211> LENGTH: 820
<212> TYPE: PRT
<213> ORGANISM: Escherichia coli
<220> FEATURE:
<223> OTHER INFORMATION: homoserine dehydrogenase fused with aspartate
      kinase

<400> SEQUENCE: 29
```

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

```
Gly Asn Glu Lys Gly Glu Leu Val Leu Gly Arg Asn Gly Ser Asp
        195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Phe Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Asn Asn Asp Asp Ala
        435                 440                 445

Thr Thr Gly Val Arg Val Thr His Gln Met Leu Phe Asn Thr Asp Gln
450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605
```

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
    690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
        755                 760                 765

Phe Lys Val Lys Asn Gly Glu Asn Ala Leu Ala Phe Tyr Ser His Tyr
    770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820

<210> SEQ ID NO 30
<211> LENGTH: 309
<212> TYPE: PRT
<213> ORGANISM: Escherichia coli
<220> FEATURE:
<223> OTHER INFORMATION: homoserine O-succinyltransferase
      with GenBank Accession No. AP 004514

<400> SEQUENCE: 30

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

-continued

```
Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
                180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His His Asn Asp Pro Gln Asn Thr
                260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
    290                 295                 300

Asn Pro Thr Leu Asp
305
```

MICROORGANISM PRODUCING L-METHIONINE PRECURSOR AND THE METHOD OF PRODUCING L-METHIONINE PRECURSOR USING THE MICROORGANISM

BACKGROUND

Methionine is one of essential amino acids of human body which has been widely used as feed and food additives and further used as a synthetic raw material for medical solutions and medical supplies. Methionine acts as a precursor of such compounds as choline (lecithin) and creatine and at the same time is used as a synthetic raw material for cysteine and taurine. Methionine can also provide sulfur. S-adenosyl-methionine is derived from L-methionine and plays a certain role in providing methyl group in human body and also is involved in the synthesis of various neurotransmitters in the brain. Methionine and/or S-adenosyl-L-methionine (SAM) inhibits fat accumulation in the liver and artery and alleviates depression, inflammation, liver disease, and muscle pain, etc.

The in vivo functions of methionine and/or S-adenosyl-L-methionine known so far are as follows.

1) It inhibits fat accumulation in the liver and artery promoting lipid metabolism and improves blood circulation in the brain, heart and kidney (J. Hepatol. Jeon B R et al., 2001 Mar; 34(3): 395-401).

2) It promotes digestion, detoxication and excretion of toxic substances and excretion of heavy metals such as Pb.

3) It can be administered as an anti-depression agent at the dosage of 800-1,600 mg/day (Am J Clin Nutr. Mischoulon D. et al., 2002 Nov; 76(5): 1158S-61S).

4) It enhances liver functions (FASEB J. Mato J M. 2002 Jan; 16(1): 15-26) and particularly is effective in the liver disease caused by alcohol (Cochrane Database Syst Rev., Rambaldi A., 2001; (4): CD002235).

5) It has anti-inflammatory effect on bone and joint diseases and promotes joint-recovery (ACP J Club. Sander O., 2003 Jan-Feb; 138(1): 21, J Fam Pract., Soeken K L et al., 2002 May; 51(5): 425-30).

6) It is an essential nutrient for hair. It provides nutrition to hair and thereby prevents hair loss (Audiol Neurootol., Lockwood D S et al., 2000 Sep-Oct; 5(5): 263-266).

Methionine can be chemically or biologically synthesized to be applied to feed, food and medicines, In the chemical synthesis, methionine is mostly produced by hydrolysis of 5-(β-methylmercaptoethyl)-hydantoin. The chemically synthesized methionine has a disadvantage of only being produced as a mixed form of L-type and D-type.

In the biological systhesis, methionine is produced by method the using proteins involved in methionine synthesis. L-methionine is biosynthesized from homoserine by the action of the enzyme expressed by such genes as metA, metB, metC, metE and metH in *Escherichia coli*. Particularly, metA is the gene encoding homoserine O-succinyltransferase which is the first enzyme necessary for methionine biosynthesis, and it converts homoserine into O-succinyl-L-homoserine. O-succinylhomoserine lyase or cystathionine gamma synthase encoded by metB gene converts O-succinyl-L-homoserine into cystathionine. Cystathionine beta lyase encoded by metC gene converts cystathionine into L-homocysteine. MetE encodes cobalamine-independent methionine synthase and metH encodes cobalamine-dependent methionine synthase, both of which convert L-homocysteine into L-methionine. At this time, 5,10-methylenetetrahydrofolate reductase encoded by metF and serine hydroxymethytransferase encoded by glyA work together to synthesize N(5)-methyltetrahydrofolate providing methyl group necessary for L-methionine synthesis.

L-methionine is synthesized by a series of organic reactions by the above enzymes. The genetic modification on the above proteins or other proteins affecting the above proteins might result in the increase of L-methionine synthesis. For example, Japanese Laid-Open Patent Publication No. 2000/139471 describes a method of producing L-methionine with the *Escherichia* sp. of which thrBC and met.) genes on the genome are deleted, metBL is over-expressed and metK is replaced by a leaky mutant. Also, US Patent Publication No. US2003/0092026 A1 describes a method using a metD (L-methionine synthesis inhibitor) knock-out microorganism which belongs to *Corynerbacterium* sp. US Patent Publication No. US2002/0049305 describes a method to increase L-methionine production by increasing the expression of 5,10-methylenetetrahydrofolate reductase (metF).

The methionine produced by the biological method is L-type, which has advantages but the production amount is too small. This is because the methionine biosynthetic pathway has very tight feed-back regulation systems. Once methionine is synthesized to a certain level, the final product methionine inhibits the transcription of metA gene encoding the primary protein for initiation of methionine biosynthesis. Over-expression of metA gene itself cannot increase methionine production because the metA gene is suppressed by methionine in the transcription stage and then degraded by the intracellular proteases in the translation stage (Dvora Biran, Eyal Gur, Leora Gollan and Eliora Z. Ron: Control of methionine biosynthesis in *Escherichia coli* by proteolysis: Molecular Microbiology (2000) 37(6), 1436-1443). Therefore, many of previous patents were focused on how to free the metA gene from its feed-back regulation system (WO2005/108561, WO1403813).

US patent publication No. US2005/0054060A1 describes a method to synthesize homocysteine or methionine by modified cystathionine synthase (O-succinylhomoserine lyase) which use methylmercaptan ($CH_3SH$) or hydrogen sulfide (H2S) directly as a sulfur source, not cysteine. However, it is well understood by those in the art that cystathionine synthase can bind various methionine precursor in the cells and thereby produce by-product al high level. For example, it was reported that cystathionine synthase accumulate high levels of homolanthionin by side reaction of O-succinylhomoserine and homocystein (J. Bacteriol (2006) vol 188:p609-618). Therefore, overexpression of cystathionine synthase can reduce the efficiency Intracellular reaction due to the increase of their side reaction. In addition, this method has many disadvantages. This process uses intracellular metabolic pathways which have side reactions and feed back regulation systems. Also this process uses $H_2S$ or $CH_3SH$ which has a severe cytotoxicity to cells. Hence the methionine production yield is comparatively small.

To solve these problems, the present inventor had developed two step process comprising; first step of producing of L-methionine precursor by *E.coli* fermentation; and second step of converting L-methionine precursor into L-methionine by enzyme reaction (PCT/KR2007/003650), the contents of which is incorporated herein by reference. This two step process can solve above problems, such as cytotoxicity of sulfides, feed-back regulation by methionine and SAMe, and decomposition intermediate product by intracellular enzymes (e.g. cystathionine gamma synthase, O-succinylhoinoserine sulfhydrylase and O-acetylhoraoserine sulfydrylase). Morever, against the chemical methionine synthetic method which produce mixed form of D-methionine and L-methionine, the two step process is very efficient to produce only L-methionine selectively.

In this two step process, production yield of methionine precursor is one of the key factor for the increase of methionine procution yield. To increase the synthetic yield of methionine precursor, O-succinyl homoserine, good combination of strong aspartokinase, homoserine transferase and feed back resistant O-succinyl homoserine transferase is really important. On the above-mentioned background, the present inventors were produced a microorganism which can produce O-succinylhomoserine characterized by the followings: 1) the homoserine O-succinyltransferase activity is introduced and enhanced, wherein the homoserine O-succinyltransferase activity is feed back resistant to methionine; and 2) the aspartokinase or homoserine dehydrogenase activity (EC2.7.2.4 or 1.1.1.3) is enhanced. This strain is capable of producing high concentrations of L-methionine precursor regardless of methionine concentration in the culture medium and production of L-methionine precursor can be remarkably increased.

SUMMARY

The present invention provides a microorganism producing L-methionine precursor and a method of producing L-methionine precursor using the microorganism.

More particularly, The present invention provides a microorganism which can produce O-succinylhomoserine characterized by the followings: 1) the homoserine O-succinyltransferase activity is introduced and enhanced, wherein the homoserine O-succinyltransferase activity is resistant to methionine feed back inhibition; and 2) the aspartokinase or homoserine dehydrogenase activity (EC2.7.2.4 or 1.1.1.3) is enhanced and method of producing L-methionine precursor using the strain.

BRIEF DESCRIPTION OF THE DRAWINGS

The application of the preferred embodiments of the present invention is best understood with reference to the accompanying drawings, wherein.

DETAILED DESCRIPTION

Figure 1:
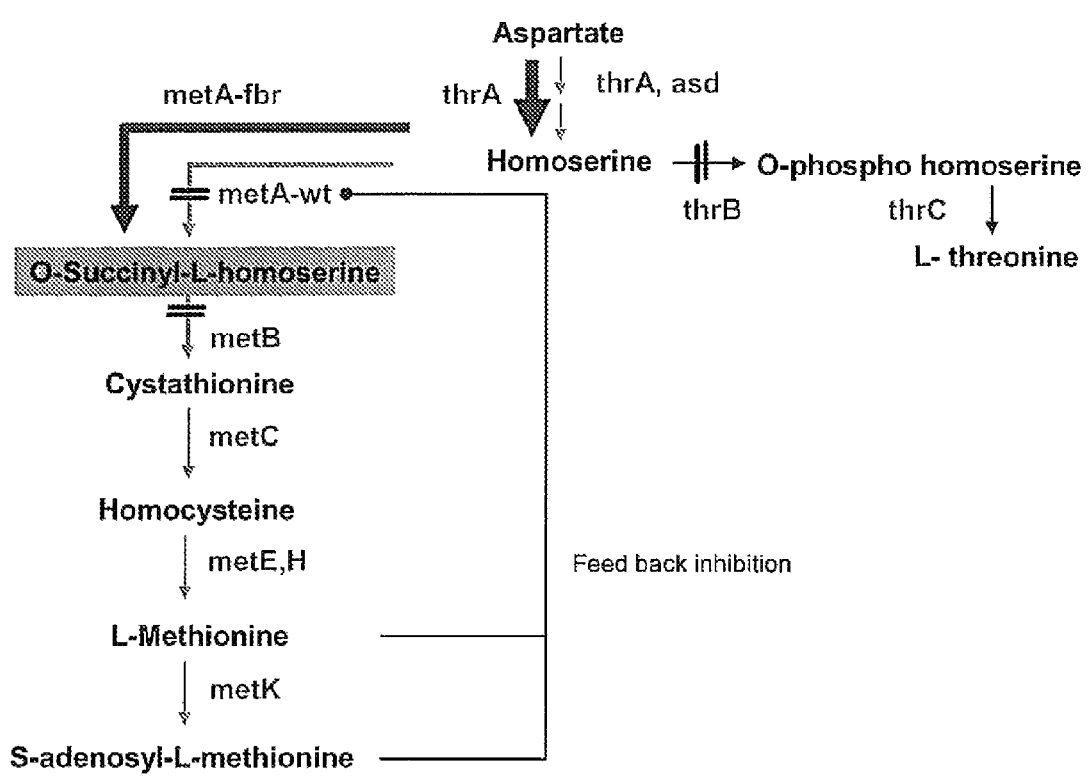
FIG. 1 is a diagram illustrating genetic manipulation of the methionine precursor producing strain.
Figure 2:
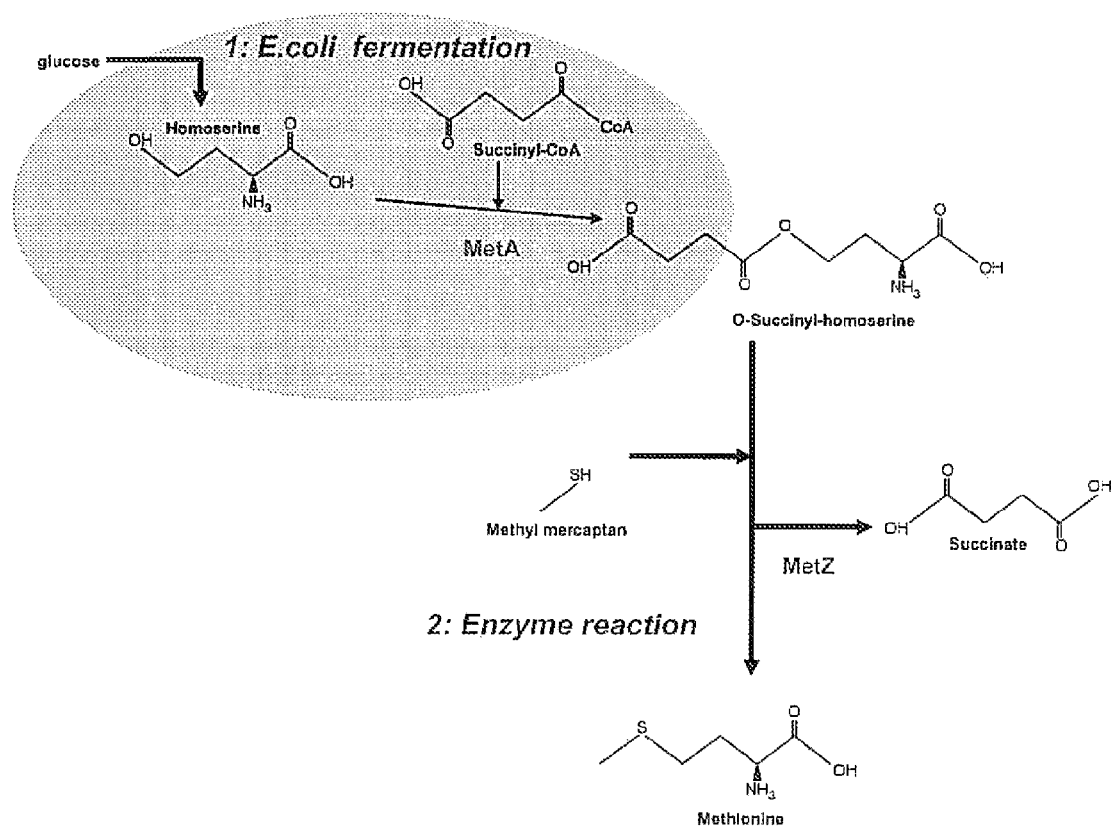
FIG. 2 is a diagram illustrating chemical structures of 2 step process for the production of methionine.

The present invention provides a microorganism overproducing O-succinylhomoserine.

In one aspect of the invention, a microorganism is a prokaryotic or eukaroytic microorganismcontaining the mutated gene encoding homoserine O-succinyltransferase, a derivative or active fragment thereof, and a subunit of homoserine O-succinyltransferase, wherein the enzyme is resistant to methionine feed back inhibition or regulation. The derivative or active fragment of homoserine O-succinyltransferase or a subunit of homoserine O-succinyltransferase maintaining the activity of the enzyme is contemplated within the scope of the present invention.

In other aspect of the invention, a microorganism is a prokaryotic or a eukaroytic microorganism containing the aspartokinase or homoserine dehydrogenase activity (EC2.7.2.4 or 1.1.1.3) which is enhanced compared to the wild type microorganism.

In one preferred aspect, the recombinant cells are *Escherichia* sp.

In accordance with an aspect thereof, the present invention is directed to a microorganism which produces L-mehtionine precursor by the followings: 1) the homoserine O-succinyltransferase activity is introduced and enhanced, wherein the homoserine O-succinyltransferase activity is resistant to a methionine feed back inhibition or regulation. And 2) the aspartokinase or homoserine dehydrogenase activity (EC2.7.2.4 or 1.1.1.3) is enhanced in the microorganism.

For purposes of the present invention, "homoserine O-succinyltransferase resistant to a methionine or methionine feedback" shall be understood to include enzymes or fragments thereof whose enzyme activity is not mitigated or downregulated by a negative feedback or negative feedback system, i.e. a negative feedback induced by a methionine or a L-methionine precursor such as O-succinyl homoserine.

In another aspect of the present invention, there are provided methods of producing L-methionine precursor using the microorganisms described herein.

The term "L-methionine precursor" is defined as metablites that are part of the methionine specific metabolic pathway or can be derived of these metabolites. Particulary, L-methionine precursor as used herein refers to a O-succinyl homoserine.

The term "L-methionine precursor-producing strain", as used herein refers to a prokaryotic or eukaryotic microorganism strain that is able to accumulate L-methionine precursor by manipulation according to the present invention. For example, the strain includes *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp. and *Norcardia* sp. microorganisms or fungi or yeasts. Preferably, the microorganisms of *Escherichia* sp., *Corynebacterium* sp., *Leptospira* sp. and yeasts can be used to produce O-Succinylhomoserine. More preferably, the microorganisms of *Escherichia* sp. can be used, and most preferably *Escherichia coli* (hereinafter reffered to as "*E.coli*") can be used.

In one aspect of the invention, the present invention provides an L-methionine precursor producing strain in which a gene involved in the decomposition or degradation of authentic or endogenous O-succinylhomoserine or O-acetyl homoserine is deleted, inactivated or weakened and instead a gene involved in the synthesis of O-succinylhomoserine which is feed back resistant is introduced or enhanced. The present invention also selectively provides a strain in which threonine biosynthesis pathway is suppressed, blocked, inhibited or weakened to enhance O-succinylhomoserine production. The present invention further provides a strain in which aspartokinase or homoserine dehydrogenase is overexpressed or activity-enhanced. The present invention also provides a strain in which homoserine O-succinyltransferase free from feed back regulation system is introduced, overexpressed and activity-enhanced and aspartokinase or homoserine dehydrogenase is over-expressed or activity-enhanced.

In one preferred aspect of the invention, the present invention provides an L-methionine precursor producing strain by deleting metB gene involved in the decomposition of L-methionine precursor, thrB gene involved in threonine biosynthesis pathway and metJ gene regulating the transcription of L-methionine precursor production genes. The present invention also provides an L-methionine precursor producing strain by knocking-out authentic metA or metX gene involved in the synthesis of methionine precursor and by introducing a feed back resistant metA. The present invention also provides an L-methionine precursor producing strain by enhancing the activity encoded by the thrA gene.

More preferably, the present invention also provides an L-methionine precursor producing strain by knocking-out authentic or endogenous metA or metX gene, introducing an mutant feed back resistant metA gene, and by enhancement of the thrA gene. The metA genes which are feed back resistant are confirmed in the former patent (PCT/KR2007/003650), the contents of which are incorporated herein by reference.

In the present invention, "inactivation" or "suppression" as used herein refers to a deletion or an attenuation of the gene. A deletion of the gene is performed by cutting out of a region of the gene or modifying the protein sequence by introducing a specific gene sequence on the chromosome. The term "attenuation", "suppressing" or "weakening" in this connection describes the reduction or elimination of the intracellular activity of one or more enzymes (proteins) in a microorganism which are encoded by the corresponding DNA, for example by reducing the activity of the protein by modifying a promoter region of the gene and the nucleotide sequence of 5'-UTR or by introducing the mutation in the ORF region of the target gene. To achieve an attenuation, for example, expression of the gene or the catalytic properties of the enzyme proteins can be reduced or eliminated. The two measures can optionally be combined.

The reduction in gene expression can take place, for example, by suitable culturing, by genetic modification (mutation) of the signal structures of gene expression or also by the antisense-RNA technique known in the art without undue experimentation. Signal structures of gene expression are, for example, repressor genes, activator genes, operators, promoters, attenuators, ribosome binding sites, the start codon and terminators. The expert can find information in this respect, inter alia, for example, in Jensen and Hammer (Biotechnology and Bioengineering 58: 191 195 (1998)), in Carrier and Keasling (Biotechnology Progress 15: 58 64 (1999)), Franch and Gerdes (Current Opinion in Microbiology 3: 159 164 (2000)) and in known textbooks of genetics and molecular biology, such as, for example, the textbook of Knippers ("Molecular Genetics", 6th edition, 1995) or that of Winnacker ("Genes and Clones", 1990), the contents of each of which are incorporated herein by reference.

Mutations which lead to a change or reduction in the catalytic properties of enzyme proteins are known from the prior art. Examples which may be mentioned are the works of Qiu and Goodman (Journal of Biological Chemistry 272: 8611 8617 (1997)), Yano et al. (Proceedings of the National Academy of Sciences, USA 95: 5511 5515 (1998)), and Wente and Schachmann (Journal of Biological Chemistry 266: 20833 20839 (1991)). Summarizing descriptions can be found in known textbooks of genetics and molecular biology, such as e.g. that by Hagemann ("General Genetics", 1986), the contents of each of which are incorporated herein by reference.

Possible mutations are transitions, transversions, insertions and deletions. Depending on the effect of the amino acid exchange on the enzyme activity, "missense mutations" or nonsense mutations are referred to. Insertions or deletions of at least one base pair in a gene lead to "frame shift mutations", which lead to incorrect amino acids being incorporated or translation being interrupted prematurely. If a stop codon is formed in the coding region as a consequence of the mutation, this also leads to a premature termination of the translation. Deletions of several codons typically lead to a complete loss of the enzyme activity, Instructions on generation of such mutations are prior art and can be found in known textbooks of genetics and molecular biology, such as e.g. the textbook by Knippers ("Molecular Genetics", 6th edition, 1995), that by Winnacker ("Genes and Clones", 1990) or that by Hagemann ("General Genetics", 1986), the contents of each of which are incorporated herein by reference.

Suitable mutations in the genes, such as, for example, deletion mutations, can be incorporated into suitable strains by gene or allele replacement.

In the present invention, the term "enhancement" describes the increase in the intracellular activity of an enzyme which is encoded by the corresponding DNA. The enhancement of intracellular activity of an enzyme can be achieved by the overexpression of the gene. Overexpression of the target gene can be acheieved by modifying the promoter region of the gene or the nucleotide sequence of the 5'-UTR region. Overexpression of the target gene can also be acheieved by introducing the extra copy of the target gene on the chromosome, by transforming the host strain with the vector containing the target gene with a promoter, or by introducing the mutation which can increase the expression in the target gene. The enhancement of the intracellular activity of an enzyme can also be achieved by introducing the mutation in the ORF region of the target gene. By enhancement measures, the activity or concentration of the corresponding protein is in general increased by at least about 10%, preferably i.e. at least about 25%, 50%, 75%, 100%, 150%, 200%, 300%, 400% or 500%, up to a maximum of 1000% or 2000%, based on that of the wild-type protein or the activity or concentration of the protein in the starting microorganism.

In a preferred embodiment of the present invention, the method for preparing an L-methionine precursor producing strain is as follows;

In step 1, a gene encoding such proteins as cystathionine gamma synthase, O-succinylhomoserine sulfhydrylase or O-acetylhomoserine sulfhydrylase is deleted or weakened in a strain in order to accumulate. L-methionine precursor such as O-succinylhomoserine or O-acetyl homoserine.

The gene encoding cystathionine gamma synthase is indicated as metB, the gene encoding O-succinylhomoserine sulfhydrylase is indicated as metZ, and the gene encoding O-acetylhomoserine sulfhydrylase is indicated as metY. A gene encoding the protein having the above mentioned activity is exemplified by metB in *Escherichia coli*. The genomic sequence of the gene can be obtained from the genomic sequence of *E. coli* (Accession no. AAC75876) informed in the previous report (Blattner et. al., Science 277: 1453-1462 (1997)). The above genomic sequence also can be obtained from NCBI (National Center for Biotechnology Information) and DDBJ (DNA Data Bank Japan). Other genes having the same activity are exemplified by metB and metY derived from *Corynebacterium*, and metZ derived from *Pseudomonas*.

Cystathionine gamma synthase or O-succinylhomoserine sulfhydrylase or O-acetylhomoserine sulfhydrylase has the activity to convert O-succinylhomoserine or O-acetylhomoserine into cystathionine or homocysteine as shown in the following reaction formulas. Therefore, where a gene having this activity is deleted or weakened, O-succinylhomoserine or O-acetylhomoserine is excessively accumulated in the culture solution.

L-cysteine+O-succinyl-L-homoserine<=>succinate+cystathionine

L-cysteine+O-acetyl-L-homoserine<=>acetate+cystathionine

HS⁻+O-succinyl -L-homoserine<=>succinate+homocysteine

HS⁻+O-acetyl-L-homoserine<=>acetate+homocysteine

In step 2, thrB gene of encoding homoserine kinase in the strain prepared in step 1 is deleted or weakened. The thrB gene is involved in the synthesis of O-phosphohomoserine from homoserine, which is then converted into threonine by thrC gene. The thrB gene is deleted or weakened in order to use all the intraceluller homoserine for the synthesis of methionine precursor.

In step 3, a transcription regulator of methionine synthetic pathway is deleted or weakened. The metA, metB, metC, metE, and metF gene involved in the methionine synthesis is repressed by feed-back regulation system. The metJ gene is a typical transcription regulator gene in E.coli. To let the metA gene be over-expressed to synthesize methionine precursor, metJ needs to be eliminated. Therefore, if metJ gene is eliminated in E. coli the metA gene expression is always increased, leading to the mass-production of L-methionine precursor.

The above steps 2 and 3 can be modified or eliminated according to a precursor producing strain. However, it can be more preferably executed to enhance the precursor production pathway in the microorganism of Escherichia sp.

In step 4, feed-back resistant homoserine O-succinyltransferase, which mediates the first process of methionine biosynthesis pathway is introduced. metA is a common designation of gene encoding the protein having activity of homoserine O-succinyltransferase. Feed back resistant homoserine O-succinyl activity is resulted from the mutatnt feed back resistant metA gene. PCT/US2007/009146 discloses the method for preparing feed-back resistant metA gene. The contents of which are incorporated herein by reference. The general information contained in the above International Patent can be included in the scope of the present invention by claims. In present invention, the amino acid sequence encoding by feed-back resistant metA 10 gene is represented in SEQ. ID. NO: 14, by the metA 11 gene is represented in SEQ. ID. NO: 16, by metA 32 gene is represented in SEQ. ID. NO: 18, by metA 37 gene is represented in SEQ. ID. NO: 20, by metA 41 gene is represented in SEQ. ID. NO: 22 (PCT/US2007/009146). Also, the present invention comprises homoserine O-succinyltransferase peptide with GenBank Accession No: AAC76983 (SEQ ID NO: 30) that has mutations in amino acid position 24, 29, 79, 114, 140, 163, 222, 275, 290, 291, 295, 297, 304, 305, or a combination thereof.

The introduction or enhancement of the metA gene resistant lo feedback inhibition is performed by introducing the gene or by modifying a promoter region of the gene and the nucleotide sequence of 5'-UTR or by introducing the mutation in the ORF region of the target gene. The introduction of a mutant metA gene which is free from feedback regulation system results in the increase of L-methionine precursor synthesis regardless of methionine concentration in the culture medium.

Morever, O-succinylhomoserine production can be more increased by deleting the authentic or endogenous metA gene in the chromosome and then introducing a mutant metA gene thereto. Feed back resistant metA gene under the metA promoter which enhanced by deleting metJ gene can produce more O-succinylhomoserine.

In step 5, aspartokinase or homoserine dehydrogenase is activity-enhanced to increase synthesis of homoserine, precursor of O-succinylhomoserine. The thrA is a common designation of gene encoding the peptide having activity of aspartokinase and homoserine dehydrogenase. The enhancement of thrA activity is performed by introducing the mutation in the thrA gene or by the multiple integration of the thrA gene on the chromosome or by introducing the plasmid containing the thrA gene.

Preferably, an aspartokinase and homoserine dehydrogenase is encoded by the gene from Unipro database No: AP_000666 (E.coli thrA). More preferably, the amino acid sequence encoding by the thrA gene is represented in SEQ. ID. NO: 29 that has mutation at amino acid position 345, the contents of which are incorporated herein by reference. Modification and enhancement of the thrA is performed by introducing the mutation in the thrA gene or by further introducing the target gene on the chromosome or by further introducing processed plasmid.

O-succinylhomoserine which is L-methionine precursor, can be accumulated in a strain by taking advantage of a part or the entire process of the above step 1 to step 5.

The L-methionine precursor producing strain can be prepared from the strain producing L-lysine, L-threonine or L-isolcucine or a combination thereof. Preferably, it can be prepared by using the L-threonine producing strain. With this strain, homoserine synthesis is going easier and the production of methionine precursor is resultantly increased. So, methionine precursor can be accumulated by deleting or weakening a gene involved in threonine biosynthesis pathway and then metA or metY or metZ gene, using the L-threonine producing strain. It is more preferred to delete or weaken thrB gene first and then metB, metY or metZ to synthesize methionine precursor.

The term, "L-threonine-producing strain" of the invention refers to a prokaryotic or eukaryotic microorganism strain that is able to produce L-threonine in vivo. For example, the strain can be include L-threonine producing microorganism strains belongs to Escherichia sp., Erwinia sp., Serratia sp., Providencia sp., Corynebacterium sp. and Brevibacterium sp. Among these, Escherichia sp. microorganism is preferred and Escherichia coli is more preferred.

In a preferred embodiment of the present invention, CJM002, the L-threonine producing and L-methionine-independent strain transformed from TF4076 (KFCC 10718, Korean Patent No. 92-8365), incorporated herein by reference, the L-threonine producing E.coli mutant strain, was used. TF4076 has a requirement for methionine, and is resistant to methionine analogues (ex, α-amino-β-hydroxy valeric acid, AHV), lysine analogues (ex, S-(2-aminoethyl)-L-cysteine, AEC), and isoleucine analogues (ex, β-aminobutylic acid). The TF4076 is not able to synthesize methionine in vivo because it is the strain which has a requirement for methionine. To use this strain as the methionine precursor producing strain of the invention by free from a requirement for methionine, the present inventors prepared the L-threonine producing strain E.coli CJM002 free from the requirement for methionine by artificial mutation using NTG. The E.coli CJM002 was named as Escherichia coli MF001 and deposited at KCCM (Korean Culture Center of Microorganism, Eulim Buld., Hongje-1-Dong, Seodaemun-Ku, Seoul, 361-221, Korea) on Apr. 9, 2004 (Accession No: KCCM-10568). In the present invention, the metB, thrB, metJ and metA gene of the E.coli CJM002 were deleted, then the feed back resistant metA gene was introduced. The result L-methionine precursor producing strain constructed using E.coli CJM002 was named CJM-A11. The Escherichia coli CJM-A11, O-succinyl homoserine producing strain, prepared by the above method was deposited at KCCM (Korean Culture Center of Microorganism, Eulim Buld., Hongje-1-Dong, Seodaemun-Ku, Seoul, 361-221, Korea) on Jan. 23, 2008, with the accession No. KCCM 10922P.

The CJM-A11 strain was transformed with the thrA expression vector, and was named CJM-A11 (pthrA(M)-CL).

In another preferred embodiment of the present invention, FTR2533 which is the L-threonine producing strain disclosed in PCT/KR2005/00344, incorporated herein by reference, was used. FTR2533 was derived from Escherichia coli TFR7624 which was derived from Escherichia coli Accession No. KCCM10236. And Escherichia coli Accession No. KCCM 10236 which was derived from Escherichia coli TF4076. Escherichia coli Accession No. KCCM 10236 is, capable of expressing higher levels of the ppc genes catalyzing the formation oxaloacetate from PEP and the enzymes necessary for threonine biosynthesis from aspartate e.g. thrA: aspartokinaze 1-homoserine dehydrogenase, thrB: homoserine kinase, thrC: threonine synthase, thereby enabling an increase in L-threonine production. And Escherichia coli FTR7624(KCCM10538) have an inactivated tyrR gene which regresses the expression of tyrB gene necessary for L-threonine biosynthesis. And *Escherichia coli* FTR2533 (KCCM10541), deposited at KCCM (Korean Culture Center of Microorganism, Eulim Buld., Hongje-1-Dong, Seodaemun-Ku, Seoul, 361-221, Korea) on Dec. 4, 2003, is the L-threonine producing strain having an in-activated galR gene, the L-threonine producing *E.coli* mutant strain.

In the present invention, the metB, thrB, metJ and metA gene of the *E.coli* FTR2533 were deleted, then the feed back resistant metA gene was introduced. The result L-methionine precursor producing strain constructed using *E.coli* FTR2533 was named CJM2-A11. The *Escherichia coli* CJM2-A11 was deposited at KCCM (Korean Culture Center of Microorganism, Eulim Buld., Hongje-1-Dong, Seodaemun-Ku, Seoul, 361-221, Korea) on Feb. 12, 2008, with the accession No. KCCM 10924P.

The CJM2-A11 strain was transformed with the thrA expression vector, and was named CJM2-A11 (pthrA(M)-CL).

In another aspect, the present invention provides a method of producing L-methionine precursor, the method includes: a) fermentation of the above microorganisms described herein; b) enrichment of the L-methionine precursor in the medium or in the microorganisms.

Alternatively, the method includes a) culturing the recombinant cell described herein and isolating O-succinylhomoserine. Any standard methods of culture and isolation known in the art can be contemplated within the scope of the present invention.

The culture of the L-methionine precursor producing strain prepared above can be performed by a proper medium and conditions known to those in the art. It is well understood by those in the art that the culture method can be used by easily adjusting, according to the selected strain. For example, the culture method includes, but not limited to batch, continuous culture and fed-batch. A variety of culture methods are described in the following reference; "Biochemical Engineering" by James M. Lee, Prentice-Hall International Editions, pp 138-176.

The medium has to meet the culture conditions for a specific strain. A variety of microorganism culture mediums are described in the following reference: "Manual of Methods for General Bacteriology" by the American Society for Bacteriology, Washington D.C., USA, 1981. Those mediums include various carbon sources, nitrogen sources and trace elements. The carbon source is exemplified by carbohydrate such as glucose, sucrose, lactose, fructose, maltose, starch, cellulose: fat such as soybean oil, sunflower oil, castor oil and coconut oil; tatty acid such as palmitic acid, stearic acid, and linoleic acid; alcohol such as glycerol and ethanol; and organic acid such as acetic aid. One of these compounds or a mixture thereof can be used as a carbon source. The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source. The medium herein can additionally include potassium dihydrogen phosphate, dipotassium hydrogen phosphate and corresponding sodium-containing salts as a phosphate source. The medium also can include a metal salt such as magnesium sulfate or iron sulfate. In addition, amino acids, vitamins and proper precursors can be added as well. The mediums or the precursors can be added to the culture by batch-type or continuous type.

PH of the culture can be adjusted during the cultivation by adding in the proper way such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas (ex, air) can be injected into the culture. The temperature of the culture is conventionally 20-45° C., preferably 25-40° C. The period of cultivation can be continued until the production of L-methionine precursor reaches a wanted level, and the preferable cultivation time is 10-160 hours.

EXAMPLES

Practical and presently preferred embodiments of the present invention are illustrative as shown in the following Examples which are set forth to illustrate, but are not to be construed as the limit of the present invention. It will be appreciated that those skilled in the art on consideration of this disclosure, may make modifications and improvements within the spirit and scope of the present invention.

Example 1

Construction of a Methionine Precursor Producing Strain

<1-1> Deletion of metB Gene

To delete the metB gene encoding cystathionine synthase in *E. coli* strain, FRT-one-step PCR deletion was performed (PNAS (2000) vol 97: P6640-6645). Primers of SEQ. ID. NO: 1 and NO: 2 were used for PCR using pKD3 vector (PNAS (2000) vol 97: P6640-6645) as a template, resulting in the construction of deletion cassette. PCR was performed as follows: 30 cycles of denaturation at 94° C. for 30 seconds, annealing at 55° C. for 30 seconds, extension at 72° C. for 1 minute.

The PCR product was electrophoresised on 1.0% agarose gel, followed by purification of DNA obtained from 1.2 kbp band. The recovered DNA fragment was electroporated into *E. coli* (K12) W3110 transformed with pKD46 vector (PNAS (2000) vol 97: P6640-6645). Before electroporation, W3110 transformed with pKD46 was cultivated at 30° C. in LB medium containing 100 μg/L of ampicilin and 5 mM of L-arabinose until $Od_{600}$ reached 0.6. Then, the cultured strain was washed twice with sterilized distilled water and one more time with 10% glycerol. Electroporation was performed at 2500 V. The recovered strain was streaked on LB plate medium containing 25 μg/L of chloramphenichol, followed by culture at 37° C. overnight. Then, a strain exhibiting resistance to chloramphenichol was selected.

PCR was performed by using the selected strain as a template with the primers No1 and 2 under the same condition. The deletion of metB gene was identified by confirming the 1.2 kb sized gene on 1.0% agarose gel. The strain was then transformed with pCP20 vector (PNAS (2000) vol 97: P6640-6645) and cultured in LB medium to eliminate the chloramphenichol marker gene. The final metB knock-out strain was constructed in which the size of metB gene reduced to 150 bp on 1.0% agarose gel by PCR under the same conditions. The constructed strain was named W3-B.

<1-2> Deletion of thrB Gene

The inventors tried to increase O-succinylhomoserine synthesis from homoserine by deletion of thrB gene encoding homoserine kinase. Particularly, when the threonine producing strain is used as a production host of O-succinylhoinoserine, deletion of thrB gene is necessary because conversion of homoserine to O-phoshohomoserine by this gene is very strong. To delete thrB gene in the W3-B strain constructed above, FRT one step PCR deletion was performed by the same manner as described above for the deletion of metB gene.

To construct thrB deletion cassette, PCR was performed by using pKD4 vector (PNAS (2000) vol 97: P6640-6645) as a template with primers of SEQ. ID. NO: 3 and NO: 4 as follows; 30 cycles of denaturation at 94° C. for 30 seconds, annealing at 55° C. for 30 seconds, extension at 72° C. for 1 minute. The PCR product was electrophoresed on 1.0% agarose gel, followed by purification of DNA obtained from 1.6 kbp band. The recovered DNA fragment was electroporated into the W3-B strain transformed with pKD46 vector. The recovered strain was streaked, on LB plate medium containing 50 μg/L of kanamycin, followed by culture at 37° C. for overnight. Then, a strain exhibiting resistance was selected.

PCR was performed by using the selected strain as a template with primers of SEQ. ID. NO: 3 and NO: 4 under the same conditions as the above. The deletion of ThrB gene was identified by selecting the strain whose size is 1.6 kb on 1.0% agarose gel. The strain was then transformed with pCP20 vector and cultured in LB medium. The final thrB knock out strain was constructed in which the size of thrB gene reduced to 150 kb on 1.0% agarose gel by PCR under the same conditions. Kanamycin marker was confirmed to be eliminated. The constructed strain was named W3-BT.

<1-3> Deletion of metJ Gene

To delete the metJ gene which is the regulator gene of the metA gene involved in methionine precursor synthesis, FRT one step PCR deletion was performed by the same manner as used for the deletion of metB gene.

To construct metJ deletion cassette, PCR was performed with primers of SEQ. ID. NO: 5 and NO: 6 as follows; 30 cycles of denaturation at 94° C. for 30 seconds, annealing at 55° C. for 30 seconds, extension at 72° C. for 1 minute.

The PCR product was electrophoresed on 1.0% agarose gel, followed by purification of DNA obtained from 1.2 kbp band. The recovered DNA fragment was electroporated into the W3-BT strain transformed with pKD46 vector. The recovered strain was streaked on LB plate medium containing chloramphenicol, followed by culture at 37° C. for overnight. Then, a strain exhibiting resistance was selected.

PCR was performed by using the selected strain as a template with primers of SEQ. ID. NO: 7 and NO: 8 under the same conditions as the above. The deletion of metJ was identified by confirming the 1.6 kb sized gene on the 1.0% agarose gel. The strain was then transformed with pCP20 vector and cultured in LB medium. The final metJ knock out strain was constructed in which the size of metJ gene reduced to 600 kb on 1.0% agarose gel by PCR under the same conditions and the strain Chloramphenicol marker was confirmed to be eliminated. The constructed strain was named W3-BTJ.

<1-4> Deletion of metA Gene

To introduce a feed back resistant metA gene in the chromosome, authentic chromosome metA gene was deleted in W3-BTJ strain. To delete the metA gene, FRT one step PCR deletion was performed.

To construct metA deletion cassette, PCR was performed with primers of SEQ. ID. NO: 9 and NO: 10 as follows; 30 cycles of denaturation at 94° C. for 30 seconds, annealing at 55° C. for 30 seconds, extension at 72° C. for 1 minute.

The PCR product was electrophoresed on 1.0% agarose gel, followed by purification of DNA obtained from 1.2 kbp band. The recovered DNA fragment was electroporated into the E. coli W3-BTJ strain transformed with pKD46 vector. The recovered strain was streaked on LB plate medium containing chloramphenicol, followed by culture at 37° C. overnight. Then, a strain exhibiting resistance was selected.

PCR was performed by using the selected strain as a template with primers of SEQ. ID. NO; 9 and NO: 10 under the same conditions as the above. The deletion of metA gene was identified by confirming 1.1 kb sized gene on 1.0% agarose gel. The strain was then transformed with pCP20 vector and cultured in LB medium. The final metA knock out strain was constructed in which the size of metA gene reduced to 100 kb on 1.0% agarose gel by PCR under the same conditions. Chloramphenicol marker was confirmed to be eliminated. The constructed strain was named W3-BTJA.

<1-5> Introduction of Feed-back Resistant metA Gene

To increase production of O-succinylhomoserine which is L-methionine precursor, overexpression of feed-back resistant metA gene encoding homoserine O-succinyltransferase was performed. PCT/US2007/009146 discloses the method for preparing feed-back resistant metA gene and activity of that.

The sequence of the feed-back resistant metA 10 gene is represented in SEQ. ID. NO: 13 and the amino acid sequence encoding by the gene is represented in SEQ. ID. NO: 14. The sequence of metA 11 gene is represented in SEQ. ID. NO: 15 and the amino acid sequence encoding by the gene is represented in SEQ. ID. NO: 16. The sequence of metA 32 gene is represented in SEQ. ID. NO: 17 and the amino acid sequence encoding by the gene is represented in SEQ. ID. NO: 18. The sequence of metA 37 gene is represented in SEQ. ID. NO: 19 and the amino acid sequence encoding by the gene is represented in SEQ. ID. NO: 20. The sequence of metA 41 gene is represented in SEQ. ID. NO: 21 and the amino acid sequence encoding by the gene is represented in SEQ. ID. NO: 22 (PCT/US2007/009146).

PCR was performed by using the above genes as a template with primers of SEQ. ID. NO: 11 and NO: 12 as follows; 25 cycles of denaturation at 94° C. for 30 seconds, annealing at 55° C. for 30 seconds, extension at 72° C. for 2 minute.

Figure 3:
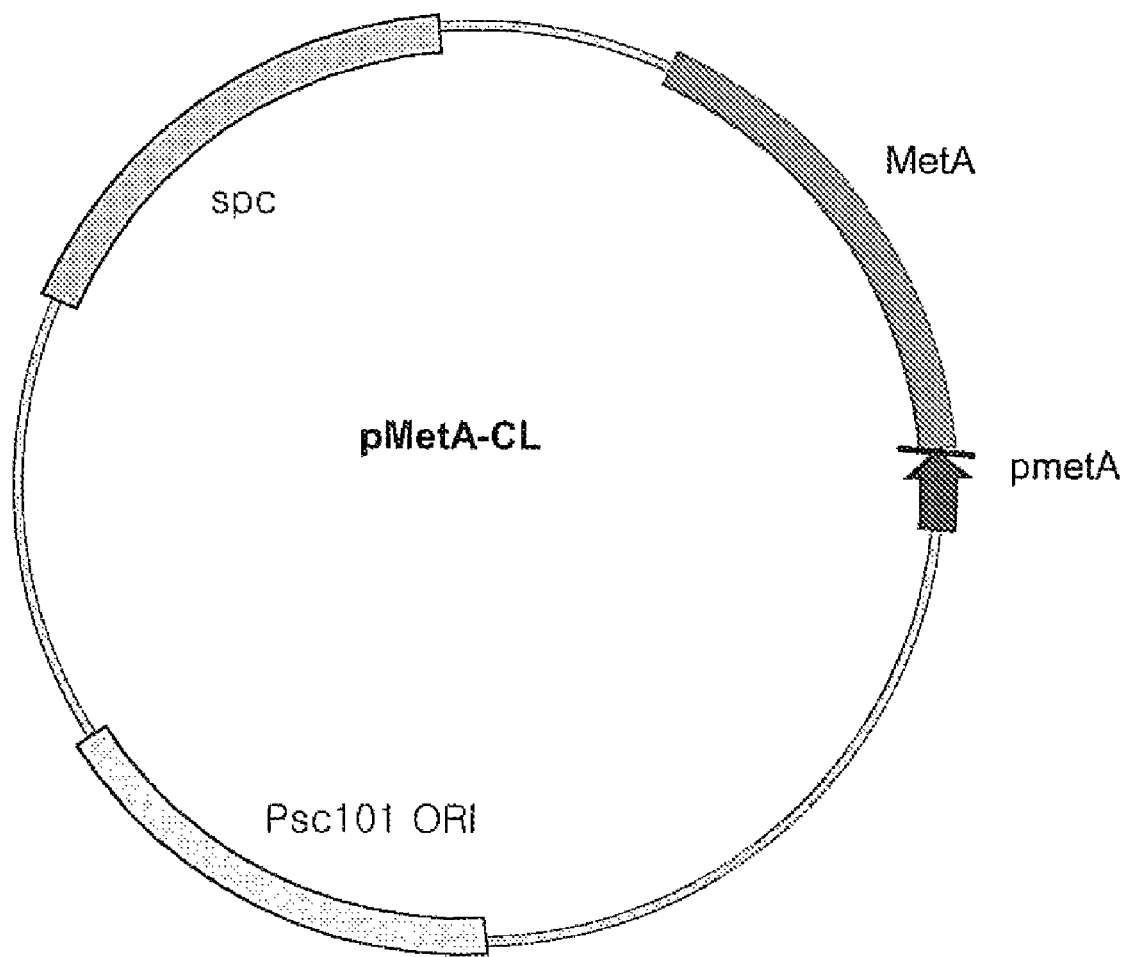
FIG. 3 is a schematic diagram of pMetA-CL for the expression of feed back resistant metA gene.

The PCR product was electrophoresed on 1.0% agarose gel, followed by purification of DNA obtained from 1.2 kbp band. Alter isolation of the DNA fragment, vector pC1.1920 was cleaved with the restriction enzyme SmaI and ligated to the isolated DNA fragment. The E.coli was transformed with the vector and plasmid-carrying cells were selected on LB agar containing 50 μg/L of spectinomycin. The constructed vector showed in FIG. 3.

The vector was electroporated into W3-BTJA strain and production capacity of the strain was checked using Erlenmeyer flask culture as described in Example 2-1, O-succinylhomoserine production of modified strain is measured, based on 100% of O-succinylhomoserine production of wild type strain. As a result, O-succinylhomoserine production of all modified strains were significantly increased than that of wild type strains, in particular, met A11, metA 10 and metA 32 show the most effective production.

TABLE 1

Feed back resistance of mutant metA in the presence of 100 mM mehtionine.

| % of specific activity retention | w.t. | #10 | #11 | #32 | #37 | #41 |
|---|---|---|---|---|---|---|
| Control | 100 | 100 | 100 | 100 | 100 | 100 |
| w/ 100 mM Met | 7.6 | 97 | 94 | 79 | 83 | 74 |

TABLE 2

O-succinylhomoserine production of Feed back resistant metA in W3-BTJA strain.

| metA | O-succinylhomoserine production (%) |
|---|---|
| wt | 100 |
| #10 | 392 |
| #11 | 425 |
| #32 | 396 |
| #37 | 227 |
| #41 | 389 |

For the stable expression of the pMetA10-CL, pMetA11-CL and pMetA32-CL showing the most efficient production, these genes were inserted into the chromosome of E.coli.

First of all, chroramphenicol maker gene was PCR-amplified by using pKD3 vector as a template with primers of SEQ. ID. NO: 23 and NO: 24. The PCR fragment was isolated by gel-elution. The metA gene was PCR-amplified with primers of SEQ. ID. NO: 9 and NO: 10. and 3'UTR region of metA gene was PCR-amplified by using W3110 wt chromosome as a template with primers of SEQ. ID. NO: 25 and NO: 26. Each PCR fragment was isolated by gel-elution and the fragment mixture was PCR-amplified with primers of SEQ. ID. NO: 9 and NO: 26, thereby metA gene fragment containing chroramphenicol maker was produced. The recovered DNA fragment was electroporated into W3BTJA strain transformed with pKD46 vector and chloramphenichol-resistent strains were selected and successful cloning of metA gene was detected using SEQ. ID. NO: 9 and NO: 10. The indentified strains which introduced modified metA gene 10, 11, 32, were named W3BTJ-A10. 11 and 32, respectively. O-succinylhomoserine production of each strain was similar to that of the W3-BTJA strain harboring each metA plasmid.

<1-6> Overexpression of thrA Gene

To increase production of O-succinylhomoserine more efficiently, overexpression of thrA gene was performed.

For this, thrA gene was PCR-amplified by using chromosome of E.coli CJM002 (KCCM10568), the L-threonine producing strain, as a template with primers of SEQ. ID. NO: 27 and NO: 28. The amplified DNA fragment was isolated by gel-elution and ligated with CJ1 promoter in pCL1920 vector using the restriction enzyme EcoRV. The E.coli was transformed with the ligated vector and plasmid-carrying cells were selected on LB agar containing 50 µg/L of spectinomycin. The vector was named pCJ-thrA(M)-CL. The amino acid sequence encoding by the thrA gene is represented in SEQ. ID. NO: 29 that has a mutation in amino acid position 345. Also, the wild type thrA gene of E.coli W3110 strain was PCR-amplified by the same manner as described above and cloned in the vector named pCJ-thrA-CL. The vectors were electroporated into W3BTJ-A11 respectively, and O-succinylhomoserine production of each strain was checked using flask culture method as described in Example 2-1. As a result, the strain transformed with the vector containing the mutant form thrA gene accumulated significantly high levels of O-succinylhomoserine.

TABLE 3

O-succinylhomoserine production in the presence of thrA expression vector.

|  | Plasmid | OSH production (%) |
|---|---|---|
| W3BTJA11 | pCL1920 | 100 |
|  | pCJ-thrA-CL | 119 |
|  | pCJ-thrA(M)-CL | 153 |

<1-7> Converting of L-Threonine Producing Strain

O-succinylhomoserine producing strain was constructed using E.coli CJM002(KCCM10568) which is the L-threonine producing and L-methionine-independent strain, as described in Example 1-1 to 1-5. The strain containing the mutant metA gene in chromosome was named CJM-A10, CJM-A11, and CJM-A32, respectively. And another L-methionine precursor producing strain was constructed using the strain FTR2533 (KCCM10541) disclosed in PCT/KR2005/00344 by the above Example 1-1 to 1-5 and named as CJM2-A11. Each strain was transformed with the thrA expression vector as described in Example 1-6. Production of methionine precursor of these strains were measured by flask culture method described in example 2-1. As a result, CJM-A11 harboring pCJ-thrA(m)-CL plasmid showed significantly higher O-succinylhomoserine production.

TABLE 4

Methionine precursor (O-succinylhomoserine) production by flask culture

|  | O-succinylhomoserine (%) |
|---|---|
| CJM-A10 | 100 |
| CJM-A11 | 113 |
| CJM-A32 | 80 |
| CJM2-A11 | 94 |
| CJM-A11 (pCJ-thrA(m)-CL) | 127 |

Example 2

Fermentation for the Production of L-methionine Precursor

<2-1> Experiment of Flask Culture

To measure the methionine precursor production of each strain constructed in Example 1, Erlenmeyer flask culture was performed. Each strain was cultured on LB plate media at 31° C. for overnight. A single colony was inoculated in 3 ml of LB medium, followed by culture at 31° C. for 5 hours. The culture solution was 200 fold diluted in 250 ml Erlenmeyer flask containing 25 ml of methionine precursor producing medium, followed by culture at 31° C., 200 rpm for 64 hours. HPLC was performed to compare with methionine precursor production capacity (Table 2 and Table 3). As a result, methionine production capacity was significantly increased in the methionine precursor-producing strain prepared from the L-threonine producing strain free from the requirement for methionine.

TABLE 1

Flask medium composition for methionine precursor production

| Composition | Concentration (per liter) |
|---|---|
| Glucose | 40 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |
| Threonine | 0.15 g |

<2-2> Large Scale Fermentation

A few strains exhibiting higher O-succinylhomoserine production capacity was selected and cultured in a 5 L fermentor to mass-produce O-succinylhomoserine. Each strain was inoculated in LB medium containing spectinomycin, followed by culture at 31° C. for overnight. Then, a single colony was inoculated in 10 ml LB medium containing spectinomycin, which was cultured at 31° C. for 5 hours. The culture solution was 100 fold diluted in 1000 ml Erlenmeyer flask containing 200 ml of methionine precursor seed medium, followed by culture at 31° C., 200 rpm for 3-10 hours. The culture solution was inoculated in a 5 L fermentor, followed by further culture for 20-100 hours by fed-batch fermentation. The methionine precursor concentration in the fermented solution was measured by HPLC and the results are shown in Table 4.

TABLE 3

Fermentor medium composition for methionine precursor production

| Composition | Seed media | Main media | Feed media |
|---|---|---|---|
| Glucose (g/L) | 10.1 | 40 | 600 |
| $MgSO_47H_2O$ (g/L) | 0.5 | 4.2 | |
| Yeast extract (g/L) | 10 | 3.2 | |
| $KH_2PO_4$ | 3 | 3 | 8 |
| Ammonium sulfate (g/L) | | 6.3 | |
| $NH_4Cl$ (g/L) | 1 | | |
| NaCl (g/L) | 0.5 | | |
| $Na_2HPO_412H_2O$ (g/L) | 5.07 | | |
| DL-Methionine (g/L) | | 0.5 | 0.5 |
| L-Isoleucine (g/L) | 0.05 | 0.5 | 0.5 |
| L-Threonine (g/L) | | 0.5 | 0.5 |

TABLE 4

Methionine precursor production in a fermentor

| | O-succinylhomoserine (g/L) |
|---|---|
| CJM-BTJ/pCJ-MetA-CL | >80 |
| CJM-A11/pCJ-thrA(M)-CL | >100 |
| CJM2-A11/pCJ-thrA(M)-CL | >90 |

INDUSTRIAL APPLICABILITY

As described hitherto, using the methionine precursor producing strain in present invention, methionine can be produced environment-friendly than conventional chemical methionine synthetic method. And the L-methionine converted from O-succinylhomoserine produced from the strain according to the present invention can be widely used in the production of animal feed or animal feed additives, in addition to human food or food additives.

---

We claim:

1. A microorganism for producing O-succinylhomoserine, comprising:
   1) a mutated homoserine O-succinyltransferase (EC2.3.1.46) which is resistant to methionine feed back inhibition or regulation,
   wherein homoserine O-succinyltransferase is represented by SEQ ID NO: 30 with Genbank Accession No. AAC76983, and the mutated homoserine O-succinyltransferase is a polypeptide having one or more amino acid mutation at a position corresponding to 79, 114, 140, 163, 222, 275, 290, 291, 304, and 305 of SEQ ID NO: 30 or a polypeptide represented by SEQ ID NO: 14, 16, 18, 20, or 22; and
   2) an aspartokinase or homoserine dehydrogenase (EC2.7.2.4 or 1.1.1.3) with enhanced activity as compared to an unmodified microorganism.

2. The microorganism of claim 1 is *Escherichia* sp.

3. The microorganism of claim 1, wherein the aspartokinase or homoserine dehydrogenase peptide has a mutation at amino acid position 345.

4. The microorganism of claim 1, wherein the aspartokinase or homoserine dehydrogenase peptide is SEQ ID NO: 29.

5. The microorganism according to claim 1, wherein the microorganism is derived from L-threonine, L-isoleucine or L-lysine producing strain.

6. The microorganism of claim 1, wherein the microorganism is *Escherichia coli*.

7. The microorganism according to claim 1, wherein the activity of cystathionine gamma synthase, O-succinylhomoserine sulfhydrylase, or O-acetylhomoserine sulfhydrylase is reduced or inactivated.

8. The microorganism according to claim 1, wherein the activity of homoserine kinase is reduced or inactivated.

9. The microorganism according to claim 1, wherein the transcription regulator of methionine synthetic pathways is weakened or inactivated.

10. The microorganism according to claim 1, wherein the endogenous homoserine O-acetyltransferase activity or the endogenous wild type homoserine O-succinyltransferase activity is reduced, suppressed or inactivated.

11. The microorganism according to claim 1, wherein the expression of metB gene encoding cystathionine gamma synthase, thrB gene encoding homoserine kinase, or metJ gene which is a transcription regulator of metA gene are reduced, suppressed or inactivated.

12. The microorganism according to claim 1, wherein the L-methionine precursor producing strain is from a threonine producing strain *Escherichia coli* MF001 free from methionine-dependency (Accession No: KCCM 10568).

13. The microorganism according to claim 1, wherein the L-methionine precursor producing strain is from a threonine producing strain *Escherichia coli* FTR2533 (Accession No: KCCM 10541).

14. The microorganism according to claim 1, wherein the L-methionine precursor producing strain is *Escherichia coli* CJM-A11(pthrA(M)-CL), prepared by transforming CJM-A11strain(KCCM 10922P) with a thrA expression vector.

15. The microorganism according to claim 1, wherein the L-methionine precursor producing strain is *Escherichia coli* CJM2-A11 (pthrA(M)-CL), prepared by transforming CJM 2-A11strain(KCCM 10924P) with a thrA expression vector.

16. The microorganism according to claim 1, wherein a biosynthetic pathway of threonine is suppressed.

17. The microorganism according to claim 1, wherein the gene expression of metA, metB, metJ, metY, metZ, thrB or in combination is suppressed.

18. The microorganism according to claim 1, wherein the gene expression of thrA is enhanced.

19. A method of producing O-succinylhomoserine, comprising:
 a) culturing the microorganism of claim 1; and
 b) isolating O-succinyl homoserine from the medium.

20. A method of producing O-succinylhomoserine, comprising :
 a) fermenting the microorganism of claim 1; and
 b) enriching the O-succinylhomoserine in the medium or in the microorganisms.

* * * * *